(12) United States Patent
Holzner

(10) Patent No.: US 6,479,456 B1
(45) Date of Patent: Nov. 12, 2002

(54) ANTIMICROBIAL PERFUME COMPOSITIONS

(75) Inventor: Günter Holzner, Grand-Lancy (CH)

(73) Assignee: Firmenich SA, Geneva (CH)

( * ) Notice: Subject to any disclaimer, the term of this patent is extended or adjusted under 35 U.S.C. 154(b) by 104 days.

(21) Appl. No.: 09/602,075

(22) Filed: Jun. 23, 2000

(51) Int. Cl.⁷ .......................... A61K 7/46; A01N 25/00
(52) U.S. Cl. .......................... 512/1; 424/401; 424/405; 514/156; 514/162; 514/859
(58) Field of Search .............. 512/1; 424/405, 424/401; 514/156, 162, 859

(56) References Cited

U.S. PATENT DOCUMENTS

| | | |
|---|---|---|
| 5,420,104 A | 5/1995 | Holzner et al. ................ 512/2 |
| 5,759,974 A | 6/1998 | Menke et al. ................ 510/191 |
| 6,294,186 B1 * | 9/2001 | Beerse et al. ................ 424/405 |

FOREIGN PATENT DOCUMENTS

| | | |
|---|---|---|
| EP | 0 433 132 | 6/1991 |
| EP | 0 451 889 | 10/1991 |
| GB | 1 401 550 | 7/1975 |
| WO | WO 92/18100 | 10/1992 |
| WO | WO 93/25185 | 12/1993 |
| WO | WO 95/15146 | 6/1995 |
| WO | WO 98/02044 | 1/1998 |

\* cited by examiner

*Primary Examiner*—Jill Warden
*Assistant Examiner*—Monique T. Cole
(74) *Attorney, Agent, or Firm*—Winston & Strawn

(57) ABSTRACT

An antimicrobial perfume compositions that contain a perfume ingredient having antimicrobial activity of at least 80% as measured by the "agar surface coating test," the "vapor phase test," or by the "direct spray method." The active ingredient is grapefruit-pip, a fumitory extract, a fumaric acid or an ester of fumaric acid or lactic acid.

14 Claims, No Drawings

US 6,479,456 B1

ANTIMICROBIAL PERFUME COMPOSITIONS

TECHNICAL FIELD AND PRIOR ART

The present invention relates to the perfumery and cosmetics industry. It relates more particularly to the perfuming of products intended for body care or hair care, as well as the perfuming of functional products.

It enables the preparation of perfumed products the perfume of which not only gives off a pleasant odour, but is also shown to increase, synergistically, the antimicrobial activity of the product in which it is incorporated.

Numerous conventional perfuming ingredients, such as essential oils or synthetic odoriferous substances, have been tested for their antimicrobial properties against various micro-organisms. Patent No. EP-A1-0 451 889, for example, contains a description of the state of the art as regards the bactericidal activity of perfuming ingredients of natural or synthetic origin. Patent No. EP-A1-0 433 132 describes a cosmetic composition containing essential oils having an activity other than a perfuming one, namely an antibacterial and/or antifungal activity. Furthermore, patent application WO 93/25185 describes a perfumed composition containing a cationic phospholipid, a perfuming base with antimicrobial action, and a fatty alcohol, the composition having an antimicrobial activity measured by the "direct spray" method. Finally, one should cite application WO 98/02044 which discloses compositions which have a disinfectant effect and are a combination of a surface-active agent, a chelating agent and an essential oil with antimicrobial action. In view of their antimicrobial properties, it is not surprising that the selection of perfuming ingredients having antimicrobial activity and the search for perfuming compositions possessing both olfactory properties and an effective antimicrobial activity should be the subject of numerous studies.

However, the antimicrobial activity of essential oils or odoriferous substances of both natural and synthetic origin is relatively weak and is insufficiently effective for controlling micro-organisms which are or may come into contact with humans.

In this context, it should be recalled that micro-organisms such as bacteria, yeasts and fungi are found, not only on the surfaces of practically any object, but also on human skin, where they cause unpleasant odours following the decomposition of sweat and other organic substances.

For such reasons, in addition to odoriferous substances of varied origin, numerous cleaning products and body-care products often also contain bactericides, considerably increasing the antimicrobial activity of a given product.

Now, because of the new consumer trends in favour of "natural" products, there is a great need for cleaning products and above all for body-care products that are free from bactericides or which contain them in smaller concentrations than the products currently on the market.

DESCRIPTION OF THE INVENTION

The present invention provides specifically a solution to the problem explained above. Consequently, the object of the invention is an antimicrobial perfuming composition, characterised in that said composition comprises a perfuming ingredient having an antimicrobial activity of at least 80% as measured by the "agar surface coating test" (ASCT), by the "vapour phase test", or by the "direct-spray method" (DSM); and an active ingredient selected from the group consisting of grapefruit-pip extract, fumitory extract, fumaric acid, or an ester of fumaric or lactic acid.

According to several embodiments of the invention, the perfuming composition of the invention may contain one or a plurality of constituents selected from surfactants, emollients (softeners for hair and skin), antimicrobial agents, or yet 2-cyclododecylidene-1-ethanol, a compound belonging to the class of macrocyclic musks (origin: Firmenich SA, Geneva, Switzerland).

The active ingredient of the composition of the invention is typically a plant extract or a compound belonging to the active principles of plants. For example, fumaric acid is present in fumitory, being part of its active principle, as well as in many other plants. Among the esters of fumaric acid there should be mentioned particularly diethyl fumarate and digeranyl fumarate.

The perfuming ingredients suitable for use in the invention exhibit an antimicrobial activity of at least 80% as measured by the "agar surface coating test" (ASCT), by the "vapour phase test" (VPT), by the "direct-spray method" (DSM), or by a combination of these methods.

The invention also relates to a perfuming composition containing at least 40% by weight of perfuming ingredients each having an antimicrobial activity of at least 80% as measured by one of the above-mentioned methods and containing at least 0.1% of said active ingredient.

The present invention discloses original and effective test methods of selecting perfuming ingredients which have an antimicrobial action of at least 80%, over and above their perfuming activity, and also for testing the efficacy of this action in a perfuming composition or a perfumed product according to the present invention. Indeed we have discovered that a perfuming composition according to the invention containing a perfuming ingredient as defined above and a plant extract or a molecule corresponding to the active principle of the said plant inhibited the action of the above-mentioned micro-organisms.

By its anti-microbial and odoriferous properties, a perfuming composition prepared according to the invention is equally suitable for applications in fine perfumery and for the perfuming of functional products. Thus it may be used advantageously in the perfuming of various articles such as soaps, bath or shower gels, body deodorants and antiperspirants, shampoos and other hair-care products. It may also be used to perfume detergents or fabric softeners, air fresheners, cleaning products, detergent compositions or those intended for washing dishes or various surfaces, or yet toilet or WC blocks or cleaners for the WC. Surprisingly it has been found that the presence of a perfuming composition according to the invention increased the bactericidal and/or fungicidal action of various articles, detergents or fabric softeners, cleaning products, air fresheners in which they were incorporated.

The perfuming compositions of the invention may contain other constituents which have a positive or synergistic effect on the antimicrobial activity of their ingredients as cited above.

A class of optional constituents are the various kinds of surfactants. These agents are known to the person skilled in the art and include anionic, cationic, non-ionic or amphoteric surfactants, as well as phospholipids. Examples of preferred surfactants according to the invention include lauryl pyrrolidone (marketed under the name Surfadone® LP 300; origin: ISP, USA), DEA lauramide (marketed under the name Monoamide® 716; origin: Mona Ind., USA), glyceryl monolaurate, lauraminopropionic acid (marketed under the name Deriphat® 151C; origin: Henkel, Germany), o-cymen-5-ol (marketed under the name Biosol; origin: Osaka Kasei, Japan), PCA ethyl cocoyl arginate (marketed under the name CAE; origin: Ajinomoto, Japan), and octoxylglycerol (marketed under the name Sensiva SC 50; origin: Schülke & Mayr, Germany). Other preferred optional agents of the invention are the zwitterionic surfactants comprising a quaternary ammonium group, such as ricinolamidopropyl dimethylamine lactate (marketed under the name Mackalene® 216; origin: McIntyre, USA) or wheat germamidopropyl dimethylamine lactate (Mackalene® 716; origin: McIntyre, USA). Finally, it is also advantageous to use phospholipids, for example hydroxyethylcetyl dimonium phosphate (marketed under the name Luquivat® mono CP; origin: BASF, Germany), cocophosphatidyl propylene glycol dimonium chloride (phospholipid CDM) or cocoamidopropyl propylene glycol dimonium chloride phosphate (phospholipid PTC) (origin: Mona Ind. USA).

Another class of ingredients optionally present in the perfuming compositions of the invention are the emollients, substances which have a softening effect on the skin and hair. These agents are of current use in the art of body-care and hair-care products, and are known to the person skilled in the art. As preferred emollients, there can be cited here quaternium 80 (marketed under the name Abil® Quat 3474; origin: Goldschmidt AG, Germany), glyceryl ricinoleate (marketed under the name Softigen® 701; origin: Hüls Chemie, Germany), and lauryl PCA (marketed under the name Laurydone®; origin: VCIB, France). A class of preferred emollients according to the invention are the esters of fumaric acid and lactic acid. As the most highly valued substances of the invention from this class of preferred emollients one can here cite lauroyl/myristyl lactylate (marketed under the name Priazul® 2131; origin: Unichema, Netherlands), $C_{12}$–$C_{13}$ alkyl lactate (marketed under the name Cosmacol ELI®; origin: Condea, Italy), and lauryl lactate (marketed under the name Ceraphyl® 31; origin: ISP, USA).

We unexpectedly discovered that the perfuming compositions of the invention indeed demonstrate an antimicrobial activity which is clearly more pronounced than expected considering the fact that all the constituents that may be present in this composition themselves possess only weak antimicrobial activity. By appropriate mixing of the previously-mentioned substances, a synergistic effect is then observed, yielding compositions with a well-balanced antimicrobial effect, which are active against all the families of micro-organisms currently present in this type of product and use, in the skin or hair. Such an effect is difficult to achieve with the known perfuming compositions, even if they contain synthetic bactericides having a very strong antimicrobial effect.

In this context, it should be mentioned that standard bactericides are generally only active against certain bacteria. For example, the two bactericides most commonly used in cosmetic products, namely Triclocarban (3,4,4'-trichlorocarbanilide) and Triclosan [5-chloro-2-(2,4-dichlorophenoxy)-phenol] are highly active against Gram-positive bacteria, but show a weak activity against Gram-negative bacteria, particularly *Pseudomonas aeruginosa*, a virtually ubiquitous species of gram-negative bacteria. By reducing the Gram-positive bacterial flora, the bactericides mentioned above can destroy the equilibrium between these bacteria, thus triggering an increase in the population of Gram-negative bacteria, thus provoking the development of bad odours.

On the other hand, the perfuming compositions of the present invention are effective against all bacteria as well as against yeasts and fungi, and have a well-balanced antimicrobial effect.

The present invention furthermore enables the preparation of perfuming compositions which, in addition to the previously defined constituents, may contain conventional antimicrobial agents and synergistically reinforce their antimicrobial character.

We thus established that the perfuming compositions according to the invention had a synergistic effect on the antimicrobial activity of antimicrobial substances such as Zinc-Pyrion® (origin: Pyrion-Chemie, Germany) or piroctone olamine (origin: Hoechst, Germany).

Other antimicrobial agents that act synergistically with the perfuming compositions of the invention are the batericides mentioned previously, namely Triclocarban and Triclosan.

In particular, we have observed that the addition of a perfuming composition according to the present invention (in combination with fumaric acid) to body-care or cleaning products allows the concentration of Triclocarban or Triclosan in the said products to be considerably reduced to values of about a half to a quarter of the quantity normally used; an increased antimicrobial activity against certain bacteria, in particular those of the Pseudomonas type, has also often been observed by comparison with Triclocarban or Triclosan alone.

It is known from the prior art cited previously that the perfuming ingredients used in the preparation of a perfume may be selected not only for their olfactory contribution but also for their antimicrobiological action. The prior art teaches us that this action is known above all for being weak. Now, the antimicrobial activity of the articles or products defined previously, to which a perfuming composition prepared according to the method(s) of the invention is added, proves to be much more effective than the activity mentioned in the prior art.

Thus, it is a quite surprising discovery that these articles or products are capable of exhibiting such effective action against the microbial flora, simply by incorporation into them of a perfuming composition composed, in a proportion of at least 40%, of active perfuming ingredients according to the test methods of the invention and a plant extract or a substance corresponding to the active principle of this plant. Moreover, it has also been established that the perfuming ingredients selected in accordance with the methods of the present invention, possess a quite remarkable and unexpected microbicidal or microbiostatic action. Indeed, they continue to exhibit an effective antimicrobial activity despite successive washings of the agar surface infected in the ASCT method or by simple diffusion of their vapours, without applying them directly to the agar surface infected in the VPT method.

The perfuming composition according to the present invention will be added to the above-mentioned articles or products to be perfumed, in concentrations conventionally used in the art. The values of these concentrations depend on the nature of the finished perfuming article or product, as well as on the desired olfactory effect, and the person skilled in the art is able to select them as a function of these parameters. Thus the articles, perfuming products or deodorants may typically contain between 0.1% and 20% by weight of a perfuming composition prepared in accordance with the above-mentioned test methods which will be described in detail below.

According to a preferred embodiment of the invention, one utilises a perfuming composition containing at least 60% or more by weight of perfuming ingredients each exhibiting a bactericidal and/or fungicidal activity of at least 80% as measured by the method(s) described below and at least 0.5% by weight of an active ingredient selected from the above-mentioned plant extracts or compounds corresponding to the active principle of these plants. We found that better results were obtained when using perfuming ingredients with a positive response of 100% or a percentage very close to this value, to any one of the test methods according to the invention.

These perfuming ingredients and the plant extracts or respectively the corresponding compounds, may be added directly to classical perfuming base formulations to produce a perfume containing pleasant olfactory notes. The perfume thus formulated will be mixed in concentrations of between 0.1 and 20% by weight relative to the weight of the product in which it will be incorporated. Perfume concentrations of the order of 0.5 to 2% have been shown to be particularly advantageous for the fine-perfumery applications envisaged according to the invention.

The antimicrobially active perfuming ingredients are selected from various chemical classes including, for example, esters, aldehydes, alcohols, ethers, ketones, acetals, nitriles, terpenic hydrocarbons, nitrogen or sulphur-containing heterocyclic compounds, as well as essential oils of natural or synthetic origin. The choice of ingredients will be dictated by a positive response of 80% in any one or two tests envisaged, and by the desired olfactory effect.

The perfuming composition of the invention will also be able to contain other ingredients, the contribution of which to the final olfactory effect will be purely hedonic. Typically it will also contain perfuming ingredients of current use, the effect of which is highly olfactory and which, like the antimicrobial ingredients mentioned above, may be selected from the classes of chemicals already cited above. The choice of these ingredients will depend on the nature of the product to be perfumed, and of course on the individual taste of the perfume designer.

In one or other of the tests, the percentage of antimicrobial activity of the perfuming ingredient is measured relative to its efficacy in reducing the microbial flora with which it is in contact. Thus the result of the bactericidal and/or fungicidal activity, under the same conditions for the different odoriferous substances selected from the various chemical classes mentioned above or the natural or synthetic essential oils, is analysed and recorded according to the percentage of activity observed.

Consequently, since it is capable of killing the variety of micro-organisms with which it is in contact, a perfuming ingredient is microbicidal, and is advantageous when it exhibits an activity of at least 80% according to the tests considered.

The antimicrobial activity of a perfuming ingredient, of a perfuming composition defined according to the invention, or of a perfumed product is measured by the following procedure.

Whatever the chosen test according to the invention, a culture of the selected germ was set up on Petri dishes under the same test conditions in parallel with a control solution composed in general of sterilised water or of a saline solution. After the period(s) of incubation considered according to the selected test, the surface area of the dish which was free of bacteria and/or fungi was measured for both the tested compound and the control solution. By calculating a surface ratio, a relative surface value, enabling the selection of the compounds with an antimicrobial activity of at least 80% in one of these tests of effectiveness, was defined. The following germs were used in these methods: *Pityrosporum ovale, Staphylococcus aureus, Staphylococcus epidermidis, Escherichia coli, Pseudomonas aeruginosa, Candida albicans, Trichophyton mentagrophytes.*

The "vapour phase test" (VPT) makes its possible to determine the antimicrobial efficacy of the vapours of either a perfuming ingredient, or a perfuming composition, or a perfumed article, on an agar surface previously inoculated with the selected micro-organism. This method turns out to be particularly useful for measuring the antimicrobial activity of air fresheners.

The "vapour phase test" is performed as follows.

A Petri dish of about 20 mm diameter is placed in the centre of a larger Petri dish –90 mm diameter—so that, when poured into the large Petri dish, the hot nutrient gel surrounds the small dish. Once the surface of the nutrient gel has solidified, it is infected with the selected germ and 1 ml of the concentrated compound to be tested is poured into the small Petri dish. The whole is covered with the cover of the large Petri dish.

The nutrient gel is then incubated at ambient temperature or at any temperature which will allow the best possible growth of the tested germs, for a period of 72 h. The antimicrobial action of the perfuming ingredient, perfuming composition or finished perfumed product is defined according to the development of the germs after 3 days of incubation. Considerable development of the micro-organisms indicates that the vapours of the compound or composition under test are not active according to the test. If, on the other hand, no culture of the germ is found to have grown, or if no more than 20% of the surface of the Petri dish is covered by the germ, this indicates microbicidal or microbiostatic activity of the compound or composition considered.

In order to determine the specific activity as measured by the test, the small Petri dish positioned in the centre of the large one is removed with the help of sterile tweezers, the cover is replaced and the nutrient gel thus deprived of vapours of the tested compound is incubated for 72 h under the optimal conditions for growth of the selected germ.

When no microbial growth is observed after this 72-h period, it can be concluded that the tested compound vapours used previously had a good antimicrobial activity, at least 80% of positive activity, and that, consequently, the selected perfuming ingredient, perfuming composition or perfumed product has microbicidal action, namely it completely kills the germs. If, after the 72 h, microbial growth is observed, it can be concluded that the previously used vapours of the tested compound were solely microbiostatic, preventing the germs from developing. It is advisable to set up a parallel germ culture, under conditions favourable to growth, without any trace of vapours of the compound to be tested. In comparison with this culture, only the perfuming ingredient, perfuming composition or perfumed product exhibiting microbiostatic activity of at least 80% according to the test is selected.

The "agar surface coating test" makes it possible to determine the antimicrobial activity of perfumes or finished products, whether perfumed or not, after washing(s) of the tested surface.

A standard, commercially available 90-mm diameter Petri dish, pre-coated with the nutrient gel, is used. Using a Gilson automatic pipette, 0.2 ml of the culture broth (already inoculated with the selected germ and incubated at ambient temperature for 2–7 days) is deposited on the agar surface and spread uniformly over it with the aid of a glass spatula. Incubation is carried out for 3 h at 37° C., taking care to leave the Petri dish half open to allow a slight drying of the medium and a good implantation of the germs over the surface. 5 ml of an appropriate concentration of the tested product or tested agent are then deposited on the surface of the gel. For example, in order to test a shampoo, its dilution with sterilised water in a proportion of ⅙ is advisable. This approximately corresponds to a concentration of shampoo applied to wet hair. The tested product is left in contact with the infected agar surface for 30 s, after which it is removed and the agar surface is rinsed with 10 ml of sterilised water. Incubation is carried out for a minimum of 24 h at ambient temperature. Already, after this first phase of the test, one can inspect the surface of the nutrient gel and establish whether or not developments have occurred in respect of the antimicrobial action.

The tested product and the agar surface are again left in contact for 30 s under the same conditions as above, followed by the stage of rinsing and of 24-h incubation at ambient temperature, and the antimicrobial evolution is observed again after this second phase of the test. This operation is repeated a third time under the same conditions except for the fact that the surface of the nutrient gel is rinsed 3 times with 10 ml of sterilised water. According to the considered application of the invention, the tested compound is left in contact with the infected agar surface from 30 s to 5 min, then the surface is rinsed 3 times with 10 ml of distilled water. The microbicidal or microbiostatic action can be established after each phase of the test, and recorded. This method makes it possible to select the ingredients with an activity of at least 80% according to the test, and also allows to test the efficacy of the antimicrobial action of a perfuming composition or perfumed product designed according to the invention, and more particularly those which exhibit a microbicidal activity from the first or second phase of the test.

The "direct spray method" (DSM) has been described in WO 93/25185, the content of which is included here by reference. In particular, there is described this method and its use to test the bactericidal or antimicrobial efficacy of cosmetic preparations applied on the skin, especially of products such as aerosols.

According to this method, by means of a measuring aerosol valve, the ready-to-use deodorant or antiperspirant composition, or a corresponding solution of the active substances, is squirted directly on to the surface of a nutrient gel previously infected with the selected germ. The gel is then incubated at 37° C. for 24 or 48 h within the scope of the subsequent evaluation of bacteria on the treated circular surface. The antimicrobial action of the perfuming composition is then defined by evaluating the area of the bacteria-free zone, relative to the total circular area treated. We noticed that the perfumed compositions according to the invention had good antimicrobial activity when the ratio between these two surfaces was about 80% or more, when the germ-inoculated nutrient gel was treated with said composition or its active principle.

The preparation, the testing of a plurality of perfuming compositions, revealed that the best results are achieved by applying the test methods indicated above for the selection and the quantity of considered perfuming ingredients. For example, when a perfuming composition contains ingredients in a quantity below the minimum 40%, it is unlikely to have an antimicrobial action of at least 80% measured according to the test methods of the invention. Consequently, for preparation of the best perfuming compositions, the choice of the perfuming ingredients as a function of their antimicrobial activity measured in accordance with any or all of the tests of the invention, and the quantity of considered active ingredients, are equally important factors to take into account in order to achieve the best results. Thus, a perfume according to the invention is just as likely to contain perfuming ingredients of current use selected for their particular olfactory note, as ingredients exhibiting both an antimicrobial activity of at least 80% as measured according to the method(s) of the invention, and a pleasant olfactory effect, or yet ingredients principally exhibiting an antimicrobial activity as defined according to the invention.

Depending on the nature of the various products to which the perfuming composition will be incorporated, the latter can be used as it is, in the form of the solution, mixed either with an aerosol propellant, or yet with ingredients of various kinds commonly used in these products and illustrated in the examples given below.

In fact, a perfuming composition according to the invention has fairly wide-ranging applications and can in particular be advantageously used to perfume products intended for cleaning and softening textiles. It may also be incorporated in products intended for cleaning surfaces around the home (floors, tiles, crockery for example), or for disinfecting or deodorising the ambient air (air fresheners for bathrooms, toilets, cupboards, for instance), thus exerting a bactericidal and/or fungicidal action on the cleaned surfaces or by the diffusion of vapours into the ambient air.

The ASCT method is especially suitable for testing perfumed products intended for washing the skin, hair, or various surfaces in industry and in the home. It turns out to be perfectly adapted, for example, for testing a perfumed shampoo intended for hair which is washed every day and which is in contact with the shampoo for about 30 s. As stated above, we have been able to establish that perfuming ingredients exhibiting an antimicrobial activity of at least 80% as measured according to said method, could be advantageously used to prepare perfuming compositions according to the invention, that is, compositions containing at least 40% by weight of active ingredients and which have an effective antimicrobial activity. Table 1 below presents the results achieved in respect of the antimicrobial activity as measured by the ASCT method of the invention, to combat *Pityrosporum ovale* micro-organism, a fungus associated with dandruff formation on the scalp—individual perfuming ingredients tested in a shampoo and enumerated here in a non-exhaustive list. Shampoo is here understood to mean a shampoo base of any current type. By way of example, a base such as the one prepared by mixing the following ingredients may be used:

| Ingredients | Parts by weight |
|---|---|
| Texapon ® N SO[1] | 25.0 |
| Demineralised water | 58.60 |
| Kathon CG[2] | 0.10 |
| Miracare ® 2MCA/P[3] | 15.00 |
| Comperlan ® KD[4] | 1.30 |
| | 100.00 |

[1] Sodium laureth sulphate; origin: Henkel, Germany
[2] Methylchloroisothiazolinone (and) methylisothiazolinone; origin: Rohm & Haas, USA
[3] Disodium cocoamphodiacetate (and) sodium lauryl sulphate (and) hexylene gycol; origin: Rhône-Poulenc, France
[4] DEA cocamide; origin: Henkel, Germany However, it is clear that any other shampoo base may be used. It should be noted that the initials BC and BS in this table correspond respectively to the abbreviations of the terms "bactericidal" and "bacteriostatic" previously explained in the description of the tests according to the invention.

TABLE 1

| Activity against Pityrosporum ovale | Test on coated agar surface (ASCT) Short period of contact 3 × 30 seconds in 3 days | | | | |
|---|---|---|---|---|---|
| Perfuming ingredients Concentration in the | 1st Application | 2nd Application 24 h | | 3rd Application 48 h | |
| shampoo | 0.5% | 0.5% | 0.1% | 0.5% | 0.1% |
| Benzyl acetate | x | BC | BC | — | — |
| Cinnamyl acetate | x | — | BS | — | BC |
| Phenylethyl acetate | x | BC | BS | — | BC |
| Phenylpropyl acetate | x | BS | x | BC | BC |
| Prenyl acetate | x | BS | — | BC | — |
| Styrallyl acetate | x | BC | x | — | BS |
| Acetophenone | BC | — | BC | — | — |
| Cinnamic alcohol ord. | x | BC | x | — | BS |
| Special redist. anisicaldehyde | x | BC | x | — | BC |
| Benzaldehyde | x | x | x | BC | BC |
| Cinnamaldehyde | x | BC | x | — | BS |
| Methylcinnamic aldehyde | x | BC | BC | — | — |
| Methyl anisate | BC | — | BC | — | — |
| Methyl anthranilate dist. | x | BC | BS | — | BC |
| Ethyl benzoate | x | BC | BS | — | BC |
| Methyl benzoate | x | BC | BS | — | BC |
| Benzylacetone | x | — | BC | — | — |
| 2,4-Dimethyl-3-cyclohexene-1-carbaldehyde[2)] | x | x | — | BC | — |
| 4-Cyclohexyl-2-methyl-2-butanol[2)] | x | x | — | BC | — |
| Coumarin | BC | — | BC | — | — |
| γ-Decalactone | x | BC | x | — | BC |
| Dihydromyrcenol | x | x | — | BC | — |
| Bergamot essential oil | x | BC | — | — | — |
| Brazilian rosewood essential oil | x | BC | x | — | BS |
| Ceylon cinnamon synth. essential oil | x | BC | BC | — | — |
| Ceylon cinnamon essential oil | x | BC | BS | — | BC |
| Chinese cinnamon essential oil | BC | — | BS | — | BC |
| Cedar ord. essential oil | x | x | — | BC | — |
| Coriander essential oil | x | BC | x | — | BC |
| Eucalyptus essential oil | x | x | x | BC | BS |
| Green foliage essential oil | x | BC | x | — | BS |
| Cinnamon leaves essential oil | x | BC | x | — | BS |
| Clove essential oil | x | BC | x | — | BC |
| Jasmine essential oil | x | x | x | BC | BS |
| Thuja essential oil | x | x | — | BC | — |
| Eugenol | x | BS | x | BC | BS |
| Florex ®[2)] | x | BS | x | BC | BS |
| Benzyl formiate | x | BC | x | — | BC |
| Raw geraniol | x | BC | x | — | BS |
| Hedione ®[2)] | x | x | — | BC | — |
| Indolarome ®[1)] | x | BC | BS | — | BS |
| Linalol | x | x | — | BC | — |
| Purified menthone | x | BS | — | BC | — |
| Methylacetophenone | x | BC | BC | — | — |
| p-Methylphenol | x | x | x | BC | BC |
| 4-Nonanolide | x | BC | x | — | BC |
| Phenylhexanol | x | BC | x | — | BS |
| Methyl salicylate | x | BC | BS | — | BC |
| γ-Undecalactone | x | x | — | BC | — |

[1)]International Flavors & Fragrances, USA
[2)]Firmenich SA, Geneva, Switzerland
BC = Bactericidal
BS = Bacteriostatic
x = devoid of antimicrobial activity
— = not tested As the results described above reveal, the ASCT method has allowed the identification of several perfuming ingredients according to the invention which may be used to prepare a perfuming composition with particular activity against *Pityrosporum ovale* and intended to be used in a shampoo as cited previously.

As perfuming ingredients exhibiting antimicrobial activity of at least 80% as measured by the test method or methods of the invention, one can also cite absinthe, wormwood, laurel, Brazilian rosewood essential oils, hexyl acetate, ethyl vinyl ketone, rose oxide, α-pinene, ormenthyl acetate, cyclohexyl acetate, acetophenone, phenylpropionic aldehyde, bergamot synthetic essential oil and Chinese cinnamon essential oil.

The invention will be described in greater detail with the aid of the following examples.

METHODS OF CARRYING OUT THE INVENTION

EXAMPLE 1

Perfuming Composition

A perfuming composition with antimicrobial activity was prepared by mixing the following ingredients:

| Ingredients | Parts by weight |
|---|---|
| Hexyl acetate[1) 2)] | 5.0 |
| Isobornyl acetate[1)] | 8.0 |
| Linalyl acetate[1)] | 9.2 |
| Ambrox ® 1) 3) 4) | 0.3 |
| Bergamot essential oil[2)] | 18.0 |
| Camphor[1) 2)] | 2.5 |
| Cedar ord. essential oil[1)] | 8.5 |
| Tricyclo [5.2.1.0[2.6]]dec-3-en-8-yl propionate[1) 3)] | 3.5 |
| Coumarin[1)] | 4.0 |
| Dihydromyrcenol[1) 2)] | 14.0 |
| Dihydroterpineol[1) 2)] | 12.5 |
| Diphenyl oxide[1)] | 1.5 |
| 3-p-Methanone[1) 2)] | 4.0 |
| Neroloxide[1) 2)] | 0.5 |
| Tetralinol[1) 2)] | 6.5 |
| 2,4-Dimethyl-3-cyclohexene-1-carbaldehyde[1) 2) 3)] | 2.0 |
| Total | 100.00 |

[1)]Perfuming ingredient exhibiting antimicrobial activity of at least 80% as measured by the "agar surface coating test" (ASCT)
[2)]Perfuming ingredient exhibiting antimicrobial activity of at least 80% as measured by the "vapour phase test" (VPT)
[3)]Origin: Firmenich SA, Geneva, Switzerland
[4)]8,12-epoxy-13,14,15,16-tetranorlabdane The ingredients mentioned above were mixed in accordance with conventional techniques known to the person skilled in the art.

This perfuming composition showed antimicrobial activity of at least 80% as measured by the ASCT or VPT method, and can be used to prepare a perfuming composition of the invention, with other ingredients as described.

EXAMPLE 2

Perfuming Composition

A jasmine-type perfuming composition with antimicrobial activity against *Pityrosporum ovale* and intended for use in a shampoo, was prepared by mixing the following ingredients:

| Ingredients | Parts by weight |
|---|---|
| Benzyl acetate[1)] | 14.0 |
| Linalyl acetate | 5.0 |
| Cinnamic alcohol[1)] | 3.0 |

-continued

| Ingredients | Parts by weight |
|---|---|
| Phenylethyl alcohol[1] | 4.0 |
| α-Amylcinnamic aldehyde | 6.0 |
| Methyl anthranilate dist.[1] | 1.5 |
| Benzyl benzoate | 18.0 |
| Eugenol[1] | 1.0 |
| Florex ® [1] [2] | 10.0 |
| Raw geraniol[1] | 5.0 |
| Clove essential oil[1] | 0.5 |
| Hédione ® [1] [3] | 20.0 |
| Hydroxycitronellal | 2.0 |
| Indolarome ® 1) 4) | 1.5 |
| Methyl jasmonate | 1.0 |
| Linalol[1] | 7.5 |
| Total | 100.00 |

[1]Perfuming ingredient exhibiting antimicrobial activity of at least 80% as measured by the "agar surface coating test" (ASCT)
[2]6 and 7-ethylideneoctahydro-5,8-methano-2H-1-benzopyran-2-one; origin: Firmenich SA, Geneva, Switzerland
[3]Methyl 3-oxo-2-pentyl-cyclopentane acetate; origin: Firmenich SA, Geneva, Switzerland
[4]4,4a,5,9b-tetrahydro-indeno[1,2-D]-1,3-dioxin; origin: International Flavors and Fragrances, USA The ingredients mentioned above were mixed in accordance with current techniques known to the person skilled in the art.

This jasmine-type perfuming composition showed antimicrobial activity of at least 80% as measured by the ASCT method against *Pityrosporum ovale*. It can be used to prepare a perfuming composition of the invention, with other ingredients as described.

EXAMPLE 3

Perfumed Anti-dandruff Shampoo Tested Using the Agar Surface Coating Test

An anti-dandruff shampoo with antimicrobial activity, intended to be used for frequent washing, was prepared with the aid of the following ingredients:

| | Ingredients | Shampoo I Parts by weight | Shampoo II Parts by weight |
|---|---|---|---|
| A | Texapon ® NSO[1] | 25.00 | 25.00 |
|   | Octopirox ® [2] | 0.60 | 0.60 |
| B | Demineralised water | 57.10 | 57.90 |
|   | Fumaric acid | 0.20 | 0.20 |
| C | Miranol ® 2MCA mod.[3] | 15.00 | 15.00 |
| D | Comperlan ® KD[4] | 1.30 | 1.30 |
| E | Perfume[5] | 0.80 | — |
|   | Total | 100.00 | 100.00 |

[1]Sodium laureth sulphate; origin: Henkel, Germany
[2]Piroctone olamine; origin: Hoechst AG, Germany
[3]Disodium cocoamphodiacetate (and) sodium lauryl sulphate (and) hexylene gycol; origin: Rhône-Poulenc, France
[4]DEA cocamide; origin: Henkel, Germany
[5]See example 1 or 2, or yet Activa 147.121X; origin: Firmenich SA, Geneva, Switzerland The Octopirox® was dissolved in the Texapon® NSO. Part B was prepared, poured into part A, and mixed. Part C was added and mixed again. Part D was added, mixed, and finally perfume E was added.

Octopirox® is a fungicide, currently used in a concentration of 0.5–1.0% in anti-dandruff preparations, having good activity against *Pityrosporum ovale* [recorded as *P. ovale* (IHEM 3967), a fungus associated with dandruff formation on the scalp]. It was observed that, during the use of a shampoo containing Octopirox®, the growth of *P. ovale* is reduced by 60% (measured according to the present test method) as compared with a shampoo without Octopirox®.

On the other hand, comparison of shampoos I and II described above has revealed that the combination of Octopirox® with the perfume and the fumaric acid according to the invention exhibits a clearly more pronounced antimicrobial activity. In fact, in the test conducted with shampoo I, total inhibition of the growth of *P. ovale* was observed. The perfumed product possessed a mean antimicrobial activity of 90% relative surface value, measured according to the "agar surface coating test".

EXAMPLE 4

Perfumed Anti-dandruff Shampoo Tested Using the "Agar Surface Coating Test"

Zinc-Pyrion®[1] is a very powerful fungicide similarly with activity against *P. ovale*. It is used in a concentration of 0.5–1.0% mainly in opaque anti-dandruff shampoos.

The following formula was tested:

| | Ingredients | Parts by weight |
|---|---|---|
| A | Demineralised water | 46.80 |
|   | Zinc-Pyrion ® | 0.60 |
|   | Gelwhite USP[2] | 1.00 |
| B | Demineralised water | 20.15 |
|   | Sodium chloride | 2.00 |
|   | Fumaric acid | 0.05 |
|   | Nutrilan ® L[3] | 1.00 |
| C | Texapon ® NSO[4] | 50.00 |
|   | Viscofil Blau BL[5]solution à 0,5% | 0.40 |
|   | Butylene glycol | 2.00 |
|   | Comperlan ® KD[6] | 2.00 |
| D | Perfume[7] | 0.80 |
|   | Total | 100.00 |

[1]Zinc-Pyrion ® ; origin: Pyrion-Chemie, Germany
[2]Origin: Euroclay, Netherlands
[3]Hydrolysed collagen; origin: Henkel, Germany
[4]Sodium laureth sulphate; origin: Henkel, Germany
[5]Origin: Sandoz, Switzerland
[6]DEA cocamide; origin: Henkel, Germany
[7]See example 1 or 2, or Activa 147.121X; origin: Firmenich SA, Geneva, Switzerland The Gelwhite was dispersed in the water under rapid agitation in a turbine. The Zinc-Pyrion was added, still under agitation.

Part B was prepared by dissolving all the compounds in the water.

Part C was prepared by mixing well to produce a homogeneous preparation.

Part A was poured into part C and mixed well with the aid of the turbine. Part B was poured into part A+C and mixed well until the shampoo was well homogenised.

The growth of *P. ovale* is completely inhibited after the 3 consecutive washings with the shampoo, the surface of the dish remaining clean. The antimicrobial activity of the perfumed shampoo is greater than 80% as measured by the ASCT method.

EXAMPLE 5

Shower Gel and Bath Foam

The following composition was tested in accordance with the "agar surface coating test" for its activity against the antimicrobial action of *Staphylococcus aureus*, in the presence and in the absence of perfume.

| Ingredients | Parts by weight |
|---|---|
| Demineralised water | 46.30 |
| Kathon CG[1] | 0.10 |
| Fumaric acid | 0.10 |
| Sodium chloride | 2.00 |
| Euperlan ® PK 771[2] | 5.00 |
| Texapon ® T42[3] | 20.00 |
| Texapon ® NSO[4] | 20.00 |
| Genaminox ® KC[5] | 5.00 |
| Perfume[6] | 1.50 |
| Total | 100.00 |

[1] Methylchloroisothiazolinone (and) methylisothiazolinone; origin: Rohm & Haas, USA
[2] Glycol distearate (and) sodium laureth sulphate (and) MEA cocamide (and) laureth-10; origin: Henkel, Germany
[3] TEA lauryl sulphate; origin: Henkel, Germany
[4] Sodium laureth sulphate; origin: Henkel, Germany
[5] Cocamide oxide; origin: Hoechst AG, Germany
[6] Composition according to example 1 or Manzana 147.038 B (1.0%) and Texan cedar essential oil (0.5%); origin: Firmenich SA Geneva, Switzerland All the ingredients were mixed in the sequence indicated, then the perfume was added.

Without perfume, the Petri dish was completely covered with a layer of the tested germ, *Staphylococcus aureus*.

After the test conducted in the presence of perfume, the surface of the Petri dish was practically clean. Only a few small colonies of the germ were observed. Thus the above shower-gel and bath-foam composition exhibits antimicrobial activity against *Staphylococcus aureus* of 85% as measured in accordance with the "agar surface coating test".

EXAMPLE 6
Shower or Bath Gel

The following composition was tested according to the "agar surface coating test" against the antimicrobial action of *Pseudomonas aeruginosa* with and in the absence of the perfume.

| Ingredients | Parts by weight |
|---|---|
| Demineralised water | 48.55 |
| Fumaric acid | 0.75 |
| Extract of fumitory | 0.10 |
| Citric acid | 0.05 |
| EDTA B (powder)[1] | 0.05 |
| Luviquat Mono CP[2] | 1.00 |
| CAE[3] | 0.40 |
| Texapon NSO 15[4] | 35.00 |
| Tego-Betain L7[5] | 5.00 |
| Plantacare 2000[6] | 4.00 |
| Kathon CG[7] | 0.60 |
| Certiol HE[8] | 2.00 |
| Perfume[9] | 1.00 |
| Sodium chloride | 2.00 |
| Total | 100.00 |

[1] Origin: BASF AG, Germany
[2] Hydroxyethyl cetyldimonium phosphate; origin: BASF AG, Germany
[3] PCA ethyl cocyl arginate; origin: Ajinomoto, Japan
[4] Sodium laureth sulphate; origin: Henkel, Germany
[5] Cocamidopropyl betaine; origin: Henkel, Germany
[6] Decyl polyglucose; origin: Henkel, Germany
[7] Mixture of ethylchloroisothiazolinone and methylisothiazolinone; origin: Rohm and Haas, USA
[8] PEG-7 glyceryl cocoate; origin: Henkel, Germany
[9] Composition according to examples 1 or 2

All the ingredients were mixed in the sequence indicated, then the perfume was added.

Without perfume, the Petri dish was completely covered with a layer of the tested germ, *Pseudomonas aeruginosa*.

After the test conducted in the presence of perfume, the surface of the Petri dish was practically clean. Only a few small colonies of the germ were observed. Thus the above shower-gel composition exhibits an antimicrobial activity against *Pseudomonas aeruginosa* measured in accordance with the "agar surface coating test".

EXAMPLE 7
Air Freshener

An air freshener with a polymeric diffusion wall and a diffusion surface area of 80 cm$^2$, containing 5 g of one of the perfumes cited in examples 1 and 2, or yet a perfume of the Cherry 20.559 type (origin: Firmenich S A, Geneva, Switzerland) and 0.5 g diethyl fumarate was placed in a 200-liter stainless-steel drum. Four Petri dishes were placed on the base beside it, each previously inoculated with a different germ. The following germs were used: *Staphylococcus aureus, Escherichia coli, Pseudomonas aeruginosa, Candida albicans*. The drum was closed and left for 3 days at ambient temperature. The same experiment, but without the air freshener, was conducted in parallel.

After 3 days of incubation it was found that the drum containing the air freshener had a pleasant odour, and no germ growth on the Petri dishes was observed.

The drum without the air freshener had, on the other hand, a strong odour of decomposition, and the dishes showed distinct bacterial growth at the surface of the agar.

EXAMPLE 8
Deodorising Soap of the Synthetic Type

| Ingredients | Parts by weight |
|---|---|
| Tensianol ® Scils[1] | 92.50 |
| Fumaric acid | 1.50 |
| Sufadone ® LP-300 | 2.00 |
| Cosmacol ® EL1 | 2.50 |
| Perfume[2] | 1.50 |
| Total | 100.00 |

[1] Sodium cocoisethionate; origin: Manro Chemicals, Great Britain
[2] Composition according to example 1, or Astéria 147.037 B (1.5%) and essence of Texan cedar (0.5%); origin: Firmenich SA, Geneva, Switzerland This mixture was extruded and pressed into pieces of soap using the usual equipment. The resulting soap was dissolved in water to a concentration of 5%. In the ASCT test conducted with the unperfumed soap, it was noticed that, following 72 h of incubation at ambient temperature, the whole surface of the Petri dish was covered with a layer of bacteria of the *Staphylococcus epidermidis* type. In the test conducted with the perfumed soap, on the other hand, it was observed that only a few colonies of the germ were distributed over the surface of the Petri dish. The perfumed soap exhibited antimicrobial activity of 80% as measured by the ASCT method.

EXAMPLE 9

Textile Softener

A textile softener was prepared from the following ingredients:

| Ingredients | Parts by weight |
|---|---|
| Praepagen ® WK[1] | 6.50 |
| 40% Formalin | 0.2 |
| Demineralised water | 91.8 |
| Colorant[2] | 0.1 |
| Fumaric acid | 0.5 |
| Digeranyl fumarate[3] | 0.2 |
| Perfume[4] | 0.7 |
| Total | 100.00 |

[1] Distearyldimethyl ammonium chloride powder; origin: Hoechst AG, Germany
[2] Colanyl blue AR/10% solution
[3] Origin: Firmenich SA, Geneva, Switzerland
[4] Composition according to examples 1 or 2

The water was heated to 60° C., the Praepagen® WK was added and mixed until it was completely dispersed. This was left to cool at ambient temperature while continuing to add the mixture. The colorant, fumaric acid, digeranyl fumarate, formalin and perfume were then added.

If the final mixture is insufficiently viscous, the viscosity may be increased by adding small quantities of NaCl. Conversely, if the mixture is too thick, the viscosity may be reduced by adding 2.5% isopropanol.

A textile softener exhibiting an antimicrobial activity was thus obtained.

EXAMPLE 10

Antimicrobial Body Deodorant

A deodorant was prepared from the following ingredients:

|   | Ingredients | Parts by weight |
|---|---|---|
| A | Citricidal ® 1) | 0.8 |
| B | Cremophor ® RH 40[2] | 2.0 |
|   | Dipropylene glycol | 14.0 |
|   | 95% Ethanol | 18.5 |
|   | Demineralised water | 61.6 |
|   | Fumaric acid | 0.5 |
| C | Phospholipid PTC | 0.6 |
|   | Softigen ® 701 | 0.5 |
| D | Perfume[3] | 1.5 |
|   | Total | 100.00 |

[1] Grapefruit pip extract; origin: BioChem, USA
[2] PEG-40 hydrogenated ricin oil; origin: BASF, Germany
[3] Composition according to Examples 1 or 2

The ingredients were mixed in accordance with the sequence indicated in the formula above. The deodorant obtained exhibited an antimicrobial activity.

EXAMPLE 11

Antimicrobial WC Block

A WC block with antimicrobial action was prepared from the following ingredients:

| Ingredients | Parts by weight |
|---|---|
| Marlon ® A 390[1] | 40.0 |
| Product AAS 90[2] | 30.0 |
| PEG 150 | 8.0 |
| Fumaric acid | 2.0 |
| Sodium sulphate | 15.0 |
| Perfume[3] | 5.0 |
| Total | 100.00 |

[1] Sodium dodecylbenzene sulphonate; origin: Hüls
[2] Isopropylaminedodecylbenzene sulphonate; origin: Henkel
[3] Composition according to Examples 1 or 2

The ingredients were mixed well in the order indicated. The product thus obtained was extruded or pressed in order to obtain a WC block exhibiting an antimicrobial activity.

EXAMPLE 12

Deodorising Cleaner for the WC

A WC cleaner was prepared from the following ingredients:

| Ingredients | Parts by weight |
|---|---|
| Demineralised water | 77.750 |
| Fumaric acid | 1.000 |
| Ethanol | 3.000 |
| Perfume | 5.000 |
| Kelzan ® ST[1] | 1.250 |
| Dobanol ® 91-8[2] | 10.000 |
| Empilan ® CDE[3] | 2.000 |
| Total | 100.00 |

[1] Xanthane gum; origin: Monsanto
[2] Ethoxylate with 8 moles of ethylene oxide based on $C_9$, $C_{10}$ and $C_{11}$ alcohols; origin: Shell
[3] DEA cocoamide; origin: Marchon, Great Britain The Kelzan® ST was added to the demineralised water under moderate stirring, and the product was then allowed to hydrate for 20 min. The perfume, the Dobanol® 91-8, the Empilan® and the ethanol were then mixed until a clear solution was obtained. The latter was added slowly to the gel obtained from the Kelzan®, under moderate stirring, until the gel restructured. After addition of the fumaric acid, a gel was obtained which lends itself to use as a WC cleaner, presenting an antimicrobial action of 100% as measured according to the ASCT test.

EXAMPLE 13

Antimicrobial Deodorising Plastic Disc for Dish-washer

A disc for dish-washer in the form of a plastic disc was prepared from the following ingredients:

| Ingredients | Parts by weight |
|---|---|
| Absorbent resin based on Pebax ® [1] or ethylene vinyl acetate | 80.00 |
| Perfume[2] | 15.00 |
| Diethyl fumarate | 5.00 |
| Total | 100.00 |

[1] Polyaminoether; origin: ATO Chimie, France
[2] Composition according to Examples 1 or 2

The ingredients identified above were mixed and placed in a mould. A deodorising disc with antimicrobial activity was thus obtained.

EXAMPLE 14
Dish-washer Liquid Product

A product for a standard dish-washer was prepared from the following ingredients:

| Ingredients | Parts by weight |
| --- | --- |
| Marlon PS 65[1] | 49.00 |
| Marlinat 242/70[2] | 11.50 |
| Marlamid DF 1218[3] | 3.00 |
| Demineralised water | 32.00 |
| Ethanol 96% by volume | 4.00 |
| Perfume[4] | 0.50 |
| Total | 100.00 |

[1] $C_{13}$–$C_{17}$ alkane sodium sulphonate; origin: Hüls, Germany
[2] Sodium laureth sulphate; origin: Hüls, Germany
[3] DEA cocoamide; origin: Hüls, Germany
[4] Composition according to examples 1 or 2, or Nicosia 115.210 or Orange 214.215; origin: Firmenich SA, Geneva, Switzerland A washing-up liquid was obtained by mixing the above-mentioned ingredients. A sample was then prepared to which 0.15% by weight of the Triclosan was added, and another sample to which 0.05% by weight of the Triclosan and 0.4% by weight of the fumaric acid were added. The two samples were tested for their antimicrobial activity against *Pseudomonas aeruginosa* in accordance with the "agar surface coating test". It was observed that, when the sample containing the Triclosan plus fumaric acid combination was used, only a few bacteria had survived on the surface of the Petri dish, whereas with the sample containing no fumaric acid, a large proportion of the surface was covered with bacteria.

EXAMPLE 15
Cleaning Product

A cleaning product was prepared form the following ingredients:

| Ingredients | Parts by weight |
| --- | --- |
| Demineralised water | 74.50 |
| Sodium carbonate | 3.00 |
| Sodium citrate | 2.00 |
| Sodium cumolsulphonate | 7.00 |
| Marlon ® A 375[1] | 10.00 |
| Tergitol 15-S-9 surfactant[2] | 3.00 |
| Perfume[3] | 0.50 |
| Total | 100.00 |

[1] Sodium dodecyl benzene sulphonate; origin: Hüls, Germany
[2] $C_{11}$–$C_{15}$ Pareth-9; origin: Union Carbide, USA
[3] DEA cocoamide; origin: Hüls, Germany
[4] Composition according to examples 1 or 2 or Nicosia 115.210 or Orange 214.215; origin: Firmenich SA, Geneva, Switzerland A cleaning product of the standard type was obtained by mixing the above ingredients. A sample was then prepared to which 0.05% by weight of the Triclosan and 0.40% by weight of the fumaric acid were added, and another sample to which 0.15% by weight of the Triclosan was added. The antimicrobial activity of these two samples was determined by means of the "agar surface coating test" against *Pseudomonas aeruginosa*. It was observed that the antimicrobial activity of the sample containing fumaric acid plus Triclosan was distinctly more pronounced than the activity of the sample containing Triclosan alone.

What is claimed is:

1. An antimicrobial perfuming composition comprising:

at least 40% by weight of perfuming ingredients each having an antimicrobial activity of at least 80% as measured by the "agar surface coating test" (ASCT) or by the "vapor phase test" (VPT); and at least 0.1% by weight of an active ingredient selected from the group consisting of grapefruit-pit extract, fumitory extract, fumaric acid, or an ester of fumaric or lactic acid.

2. A composition according to claim 1, comprising at least 60% by weight of said perfuming ingredients.

3. A composition according to claim 1, wherein each perfuming ingredient exhibits a microbial activity of 100% as measured by the "ASCT" method or by the "VPT" method.

4. A perfumed article containing an antimicrobial perfuming composition according to claim 1.

5. The perfumed article according to claim 4, in the form of a soap, a bath or shower gel, a shampoo or other hair-care product, a cosmetic preparation, a body deodorant or antiperspirant, an air freshener, a detergent or textile softener, or a cleaning product for domestic or industrial use.

6. A method of conferring, imparting or increasing the antimicrobial activity of a functional product or an article for use in body or hair care, which comprises adding to said product or article an antimicrobial perfuming composition comprising:

a perfuming ingredient having an antimicrobial activity of at least 80% as measured by the "agar surface coating test" (ASCT), by the "vapor phase test" (VPT), or by the "direct-spray method" (DSM); and an active ingredient selected from the group consisting of grapefruit-pit extract, fumitory extract, fumaric acid, or an ester of fumaric or lactic acid;

said composition being added in an amount effective to confer, impart, or increase the antimicrobial activity thereof.

7. The method of claim 6 wherein the functional product is a detergent or fabric softener, an air freshener, a household cleaning product, a dishwashing detergent or a water closet cleaner.

8. The method of claim 6 wherein the article is a soap, bath or shower gel, a deodorant, antiperspirant, or a shampoo or other hair care product.

9. The method of claim 6, wherein the antimicrobial composition comprises an antimicrobial agent selected from 3,4,4'-trichlorocarbanilide and 5-chloro-2-(2,4-dichlorophenoxy)-phenol.

10. The method of claim 6, wherein the fumaric acid ester is diethyl fumarate or digeranyl fumarate.

11. The method of claim 6, wherein the antimicrobial composition comprises a surfactant of an anionic, cationic, non ionic or amphoteric nature, or a phospholipid.

12. The method of claim 11, wherein the surfactant is a phospholipid or a quaternary surfactant.

13. The method of claim 6, wherein the antimicrobial composition comprises an emollient of current use in perfumery or cosmetics.

14. The method of claim 13, wherein the emollient is an ester of lactic or fumaric acid.

* * * * *

UNITED STATES PATENT AND TRADEMARK OFFICE
CERTIFICATE OF CORRECTION

PATENT NO.    : 6,479,456 B1                                        Page 1 of 1
DATED         : November 21, 2002
INVENTOR(S)   : Holzner It is certified that error appears in the above-identified patent and that said Letters Patent is hereby corrected as shown below:

<u>Title page,</u>
Insert the following Items:
 -- Related U.S. Application Data
 [60] Continuation of application No. PCT/IB99/01635 filed on Oct. 6, 1999. --.
-- [30] Foreign Application Priority Data
Oct. 26, 1998  (CH)……….. 2154/98 --.

<u>Column 18,</u>
Line 9, change "grapefruit-pit" to -- grapefruit-pip --.
Line 30, before "a perfuming ingredient", insert -- at least 40% by weight of --.
Line 34, before "an active ingredient", insert -- at least 0.1% by weight of --.
Lines 59-60, delete "of current use in perfumery of cosmetics".

Signed and Sealed this

Twenty-second Day of July, 2003

JAMES E. ROGAN
*Director of the United States Patent and Trademark Office*